(12) United States Patent
Haydon et al.

(10) Patent No.: US 8,415,383 B2
(45) Date of Patent: Apr. 9, 2013

(54) SUBSTITUTED BENZAMIDINES AS ANTIBACTERIAL AGENTS

(75) Inventors: David John Haydon, Oxfordshire (GB); Ian Collins, Oxfordshire (GB); Lloyd George Czaplewski, Oxfordshire (GB)

(73) Assignee: Biota Scientific Management Pty Ltd, Notting Hill, Victoria (AU)

( * ) Notice: Subject to any disclaimer, the term of this patent is extended or adjusted under 35 U.S.C. 154(b) by 0 days.

(21) Appl. No.: 12/679,334

(22) PCT Filed: Sep. 22, 2008

(86) PCT No.: PCT/GB2008/003208
§ 371 (c)(1), (2), (4) Date: Jun. 3, 2010

(87) PCT Pub. No.: WO2009/040507
PCT Pub. Date: Apr. 2, 2009

(65) Prior Publication Data
US 2010/0298388 A1    Nov. 25, 2010

(30) Foreign Application Priority Data

Sep. 25, 2007 (GB) .................................. 0718735.4

(51) Int. Cl.
A01N 43/40 (2006.01)
A61K 31/44 (2006.01)

(52) U.S. Cl.
USPC ........................................................ 514/345

(58) Field of Classification Search .................... None
See application file for complete search history.

(56) References Cited

FOREIGN PATENT DOCUMENTS

| WO | WO 9911627 A | 3/1999 |
| WO | WO 0151456 A | 7/2001 |
| WO | WO 2007107758 A | 9/2007 |

OTHER PUBLICATIONS

International Search Report for PCT/GB2008/003208 (WO/2009/040507), Issued on Dec. 17, 2008.

*Primary Examiner* — Brandon Fetterolf
*Assistant Examiner* — Jared D Barsky
(74) *Attorney, Agent, or Firm* — Banner & Witcoff, Ltd.

(57) ABSTRACT

Compounds of formula (IA) or (IB) have antibacterial activity: wherein W is =C(H)— or =N—; $R_3$ is a radical of formula -(Alk$^1$)$_m$-(Z$^1$)$_p$-(Alk$^2$)$_n$-Q wherein m, p and n are independently 0 or 1, provided that at least one of m, p and n is 1, Z1 is —O—, —S—, —S(O)—, —S(O$_2$)—, —NH—, —N(CH$_3$)—, —N(CH$_2$CH$_3$)—, —C(=O)—, —O—(C=O)—, —C(=O)—O—, or an optionally substituted divalent monocyclic carbocyclic or heterocyclic radical having 3 to 6 ring atoms; or an optionally substituted divalent bicyclic carbocyclic or heterocyclic radical having 5 to 10 ring atoms; Alk$^1$ and Alk$^2$ are optionally substituted C$_1$-C$_6$ alkylene, C$_2$-C$_6$ alkenylene, or C$_2$-C$_6$ alkynylene radicals, which may optionally terminate with or be interrupted by —O—, —S—, —S(O)—, —S(O$_2$)—, —NH—, —N(CH$_3$)—, Or —N(CH$_2$CH$_3$)—; and Q is hydrogen, halogen, nitrile, or hydroxyl, or an optionally substituted monocyclic carbocyclic or heterocyclic radical having 3 to 6 ring atoms; or an optionally substituted bicyclic carbocyclic or heterocyclic radical having 5 to 10 ring atoms; $R_4$ and $R_5$ are optional substituents; and $R_2$, $R_6$ and $R_7$ are independently hydrogen or a radical of formula -(Alk$^3$)$_x$-(Z$^2$)y-(Alk$^4$)$_z$-H wherein x, y and z are independently 0 or 1, Z$^2$ is —O—, —S—, —S(O)—, —S(O$_2$)—, —NH—, —N(CH$_3$)—, —N(CH$_2$CH$_3$)—, —C(=O)—, —O—(C=O)— or —C(=O)—O—; Alk$^3$ and Alk$^4$ are optionally substituted C$_1$-C$_3$ alkylene, C$_2$-C$_3$ alkenylene, or C$_2$-C$_3$ alkynylene radicals, which may optionally terminate with or be interrupted by —O—, —S—, —S(O)—, —S(O$_2$)—, —NH—, —N(CH$_3$)—, or —N(CH$_2$CH$_3$)—.

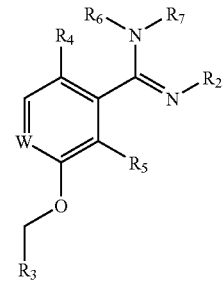

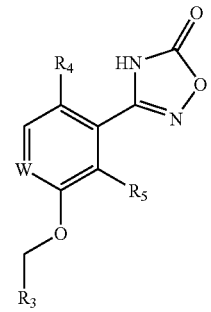

15 Claims, No Drawings

SUBSTITUTED BENZAMIDINES AS ANTIBACTERIAL AGENTS

CROSS REFERENCE TO RELATED APPLICATIONS:

This application is a National Stage application of co-pending PCT application PCT/GB2008/003208 filed Sep. 22, 2008, which claims the benefit of Great Britain application number 0718735.4 filed Sep. 25, 2007. These applications are incorporated herein by reference in their entireties.

This invention relates to the use of a class of substituted benzamidines, isonicotinamidines and structurally related phenyl and pyridinyl oxadiazolones, as antibacterial agents, to novel members of that class per se, and to pharmaceutical compositions comprising such compounds.

BACKGROUND TO THE INVENTION

Many classes of antibacterial agents are known, including the penicillins and cephalosporins, tetracyclines, sulfonamides, monobactams, fluoroquinolones and quinolones, aminoglycosides, glycopeptides, macrolides, polymyxins, lincosamides, trimethoprim and chloramphenicol. The fundamental mechanisms of action of these antibacterial classes vary.

Bacterial resistance to many known antibacterials is a growing problem. Accordingly there is a continuing need in the art for alternative antibacterial agents, especially those that have mechanisms of action fundamentally different from the known classes.

Amongst the Gram-positive pathogens, such as staphylococci, streptococci, mycobacteria and enterococci, resistant strains have evolved/arisen which make them particularly difficult to eradicate. Examples of such strains are methicillin resistant *Staphylococcus aureus* (MRSA), methicillin resistant coagulase negative staphylococci (MRCNS), penicillin resistant *Streptococcus pneumoniae* and multiply resistant *Enterococcus faecium*. In view of the rapid emergence of multidrug-resistant bacteria, the development of antibacterial agents with novel mechanisms of action that are effective against the growing number of resistant bacteria, particularly the vancomycin resistant enterococci and beta-lactam antibiotic-resistant bacteria, such as methicillin-resistant *Staphylococcus aureus*, is of utmost importance.

Cell division has been of considerable interest to the pharmaceutical industry as a target because it comprises a group of well conserved target proteins that are all essential for the viability of a wide range of bacteria, and their activities are completely different from those of the proteins involved in cell division of mammalian cells. A number of compounds that act on components of the cell division machinery have been described (Ohashi, Y. et al. J. Bacteriol. 181, 1348-1351 (1999), Jennings, L. D. et al. Bioorg Med Chem 12, 5115-5131 (2004), Sutherland, A. G. et al. Org Biomol Chem 1, 4138-4140 (2003), Margalit, D. N. et al. Proc. Natl. Acad. Sci. USA 101, 11821-11826 (2004), Wang, J. et al. J. Biol. Chem. 278, 44424-44428 (2003), White, E. L. et al. J. Antimicrob. Chemother. 50, 111-114 (2002), Reynolds, R. C. et al. Bioorg Med Chem Lett 14, 3161-3164 (2004) and Stokes et al. J Biol Chem. 280, 39709-39715 (2005)). So far, most effort has been directed at the FtsZ protein, since it has several biochemical activities that can be assayed in vitro. Unfortunately, most of the compounds described so far either have relatively low potency, undesirable pharmacological properties or unknown specificity.

BRIEF DESCRIPTION OF THE INVENTION

Our co-pending International Patent Application No. PCT/GB2007/001012 is concerned with substituted benzamides or isonicotinamides having antibacterial activity as evidenced by inhibition of bacterial growth by members of that class.

The present invention is concerned with substituted benzamidines, isonicotinamidines and phenyl and pyridyl oxadiazolones which are structurally related to the benzamides and isonicotinamides of PCT/GB2007/001012, in that the amide group of the latter has been replaced by a (substituted) amidino group or an oxadiazolone group. The present compounds exhibit activity against strains of Gram-positive bacteria, such as *staphylococci* and *bacilli*, for example *Staphylococcus aureus*, *Staphylococcus epidermidis*, *Staphylococcus haemolyticus*, *Staphylococcus saprophyticus*, *Bacillus subtilis* and *Bacillus cereus*. Whilst the invention is not limited by any particular hypothesis as to the mechanism of action of the compounds, it is presently believed that such activity is mediated by the compounds inhibiting cell division through binding to FtsZ.

DETAILED DESCRIPTION OF THE INVENTION

In its "use aspect", the present invention provides the use of a compound which is a substituted benzamidine, isonicotinamidine or phenyl or pyridyl oxadiazolone of formula (IA) or (IB), or a salt thereof, in the manufacture of a composition for the treatment of bacterial infection:

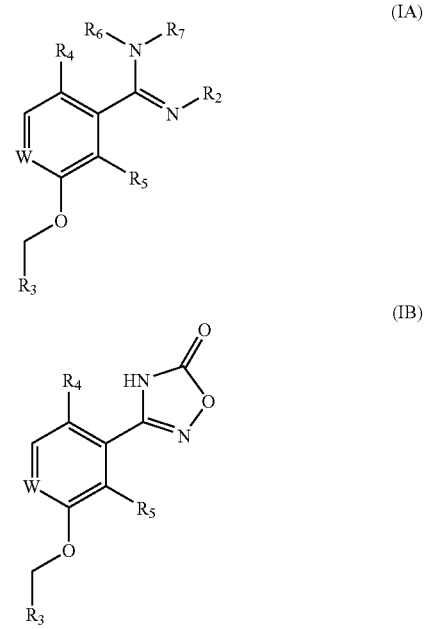

wherein
W is =C(H)— or =N—;
R$_3$ is a radical of formula -(Alk$^1$)$_m$-(Z$^1$)$_p$-(Alk$^2$)$_n$-Q
wherein
  m, p and n are independently 0 or 1, provided that at least one of m, p and n is 1,
  Z$^1$ is —O—, —S—, —S(O)—, —S(O$_2$)—, —NH—, —N(CH$_3$)—, —N(CH$_2$CH$_3$)—, —C(=O)—, —O—(C=O)—, —C(=O)—O—, or an optionally substituted divalent monocyclic carbocyclic or heterocyclic radical having 3 to 6 ring atoms; or an optionally substituted divalent bicyclic carbocyclic or heterocyclic radical having 5 to 10 ring atoms;

Alk¹ and Alk² are optionally substituted $C_1$-$C_6$ alkylene, $C_2$-$C_6$ alkenylene, or $C_2$-$C_6$ alkynylene radicals, which may optionally terminate with or be interrupted by —O—, —S—, —S(O)—, —S(O$_2$)—, —NH—, —N(CH$_3$)—, or —N(CH$_2$CH$_3$)—; and Q is hydrogen, halogen, nitrile, or hydroxyl or an optionally substituted monocyclic carbocyclic or heterocyclic radical having 3 to 6 ring atoms; or an optionally substituted bicyclic carbocyclic or heterocyclic radical having 5 to 10 ring atoms;

$R_4$ and $R_5$ are optional substituents; and $R_2$, $R_6$ and $R_7$ are independently hydrogen or a radical of formula -(Alk³)$_x$-(Z²)$_y$-(Alk⁴)$_z$-H wherein x, y and z are independently 0 or 1, Z² is —O—, —S—, —S(O)—, —S(O$_2$)—, —NH—, —N(CH$_3$)—, —N(CH$_2$CH$_3$)—, —C(=O)—, —O—(C=O)— or —C(=O)—O—;

Alk³ and Alk⁴ are optionally substituted $C_1$-$C_3$ alkylene, $C_2$-$C_3$ alkenylene, or $C_2$-$C_3$ alkynylene radicals, which may optionally terminate with or be interrupted by —O—, —S—, —S(O)—, —S(O$_2$)—, —NH—, —N(CH$_3$)—, or —N(CH$_2$CH$_3$)—.

In other broad aspects, the invention includes (i) the use of a compound (IA) or (IB) as defined above in the manufacture of a composition for treating bacterial infection.

(ii) a method of treating bacterial infection in a subject suffering such infection comprising administering to the subject an amount of a compound (IA) or (IB) as defined above, sufficient to inhibit bacterial growth;

(iii) a method of treating bacterial contamination of a substrate comprising applying to the site of such contamination an amount of a compound (IA) or (IB) as defined above, sufficient to inhibit bacterial growth;

(iv) a compound (IA) or (IB) as defined above for use in a method of treatment of the human body;

(v) a compound (IA) or (IB) as defined above for use in treating bacterial infection;

(vi) an antibacterial composition comprising a compound of formula (IA) or (IB) as defined above, and a pharmaceutically acceptable carrier.

Some members of the class of compounds defined by formulae (IA) and (IB) above are believed novel in their own right, and the invention includes all such novel members of the class. Thus, in its "compound per se aspect", the invention also includes compounds of formula (IA) or (IB) above, or salts thereof: wherein W, $R_2$, $R_6$ and $R_7$ are as defined above; $R_4$ and $R_5$ are independently fluoro or chloro, or one of $R_4$ and $R_5$ is hydrogen while the other is fluoro or chloro; and $R_3$ is a radical selected from those of formulae A-J:

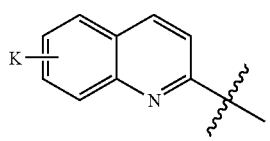

A

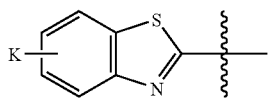

B

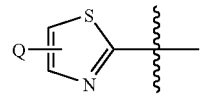

C

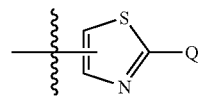

D

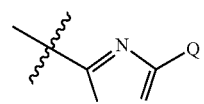

E

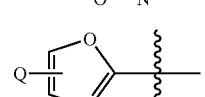

F

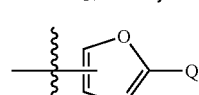

G

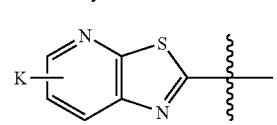

H

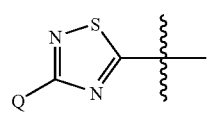

I

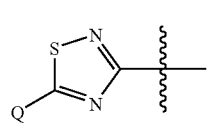

J wherein K is -(Alk²)-Q and where Alk² and Q are as defined above, and wherein any unsubstituted ring carbon is optionally substituted.

Terminology

The term "compounds with which the invention is concerned" includes compounds of formula (IA) or (IB) as defined in relation to the "use aspect" of the invention and the "compound per se aspect" of the invention.

As used herein, the term "($C_a$-$C_b$)alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein the term "divalent ($C_a$-$C_b$)alkylene radical" wherein a and b are integers refers to a saturated hydrocarbon chain having from a to b carbon atoms and two unsatisfied valences. The term includes, for example, methylene, ethylene, n-propylene and n-butylene.

As used herein the term "($C_a$-$C_b$)alkenyl" wherein a and b are integers refers to a straight or branched chain alkenyl moiety having from a to b carbon atoms having at least one double bond of either E or Z stereochemistry where applicable. The term includes, for example, vinyl, allyl, 1- and 2-butenyl and 2-methyl-2-propenyl.

As used herein the term "divalent ($C_a$-$C_b$)alkenylene radical" means a hydrocarbon chain having from a to b carbon atoms, at least one double bond, and two unsatisfied valences.

The term includes, for example, —CH═CH— (vinylene), —CH═CH—CH$_2$—, —CH$_2$—CH═CH—, —CH═CH—CH$_2$—CH$_2$—, —CH═CH—CH$_2$—CH$_2$—CH$_2$—, —CH═CH—CH═CH—, —CH═CH—CH═CH—CH$_2$—, —CH═CH—CH═CH—CH$_2$—CH$_2$—, —CH═CH—CH$_2$—CH═CH—, and —CH═CH—CH$_2$—CH$_2$—CH═CH—.

As used herein the term "C$_a$-C$_b$ alkynyl" wherein a and b are integers refers to straight chain or branched chain hydrocarbon groups having from a to b carbon atoms and having in addition at least one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent (C$_a$-C$_b$)alkynylene radical" wherein a and b are integers refers to a divalent hydrocarbon chain having from a to b carbon atoms, and at least one triple bond. The term includes, for example, —C≡C—, —C≡C—C$_2$—, and —CH$_2$—C≡CH—.

As used herein the term "cycloalkyl" refers to a monocyclic or bridged monocyclic saturated carbocyclic radical having from 3-8 carbon atoms and includes, for example, cyclopropyl, cyclobutyl, cyclopentyl, cyclohexyl, cycloheptyl, cyclooctyl and bicyclo[2.2.1]hept-1-yl.

As used herein the unqualified term "aryl" refers to a mono- or bi-cyclic carbocyclic aromatic radical. Illustrative of such radicals are phenyl and naphthyl.

As used herein the unqualified term "heteroaryl" refers to a mono-, or bi-cyclic aromatic radical containing one or more heteroatoms selected from S, N and O, and includes radicals having two such monocyclic rings, or one such monocyclic ring and one monocyclic aryl ring, which are fused or directly linked by a covalent bond. Illustrative of such radicals are thienyl, benzthienyl, furyl, benzfuryl, pyrrolyl, imidazolyl, benzimidazolyl, thiazolyl, benzthiazolyl, thiazolopyridinyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyridazinyl, triazinyl, indolyl and indazolyl.

As used herein the unqualified term "heterocyclyl" or "heterocyclic" includes "heteroaryl" as defined above, and in addition means a mono- or bi-cyclic non-aromatic radical containing one or more heteroatoms selected from S, N and O. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with up to four compatible substituents, each of which independently may be, for example, (C$_1$-C$_6$)alkyl, (C$_2$-C$_6$)alkenyl, (C$_2$-C$_6$)alkynyl, (C$_1$-C$_6$)alkoxy, hydroxy, hydroxy(C$_1$-C$_6$)alkyl, mercapto, mercapto(C$_1$-C$_6$)alkyl, (C$_1$-C$_6$)alkylthio, halo (including fluoro, bromo and chloro), fully or partially fluorinated (C$_1$-C$_3$)alkyl, (C$_1$-C$_3$)alkoxy or (C$_1$-C$_3$)alkylthio such as trifluoromethyl, trifluoromethoxy, and trifluoromethylthio, nitro, nitrile (—CN), oxo (═O), phenyl, phenoxy, monocyclic heteroaryl or heteroaryloxy with 5 or 6 ring atoms, —COOR$^A$, —COR$^A$, —OCOR$^A$, —SO$_2$R$^A$, —CONR$^A$R$^B$, —SO$_2$NR$^A$R$^B$, —NR$^A$R$^B$, OCONR$^A$R$^B$, —NR$^B$COR$^A$, —NR$^B$COOR$^A$, —NR$^B$SO$_2$OR$^A$ or —NR$^A$CONR$^A$R$^B$ wherein R$^A$ and R$^B$ are independently hydrogen or a (C$_1$-C$_6$)alkyl group or, in the case where R$^A$ and R$^B$ are linked to the same N atom, R$^A$ and R$^B$ taken together with that nitrogen may form a cyclic amino ring. Where the substituent is phenyl, phenoxy or monocyclic heteroaryl or heteroaryloxy with 5 or 6 ring atoms, the phenyl or heteroaryl ring thereof may itself be substituted by any of the above substituents except phenyl phenoxy, heteroaryl or heteroaryloxy. An "optional substituent" or "substituent" may be one of the foregoing specified groups.

As used herein the term "salt" includes base addition, acid addition and quaternary salts. Compounds with which the invention is concerned which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl)aminomethane, L-arginine, L-lysine, N-ethyl piperidine, dibenzylamine and the like. Those compounds (I) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesulfonic, glutamic, lactic, and mandelic acids and the like. For a review on suitable salts, see *Handbook of Pharmaceutical Salts: Properties, Selection, and Use* by Stahl and Wermuth (Wiley-VCH, Weinheim, Germany, 2002).

It is expected that compounds with which the invention is concerned may be recovered in the form of hydrates or solvates. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water. References herein to compounds of formula (I) are to be understood as including such compounds in the form of hydrates or solvates thereof.

Compounds with which the invention is concerned which contain one or more actual or potential chiral centres, because of the presence of asymmetric carbon atoms, can exist as a number of enantiomers or diastereoisomers with R or S stereochemistry at each chiral centre. The invention includes all such enantiomers and diastereoisomers and mixtures thereof.

Individual compounds with which the invention is concerned invention may exist in several polymorphic forms and may be obtained in different crystal habits.

So-called 'prodrugs' of the compounds with which the invention is concerned are also within the scope of the invention. Thus certain derivatives of the compounds which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and V. J. Stella) and *Bioreversible Carriers in Drug Design*, Pergamon Press, 1987 (ed. E. B. Roche, American Pharmaceutical Association; C. S. Larsen and J. Østergaard, Design and application of prodrugs, In Textbook of Drug Design and Discovery, 3$^{rd}$ Edition, 2002, Taylor and Francis).

Prodrugs in accordance with the invention can, for example, be produced by replacing appropriate functionalities present in the compounds of formula (IA) and (IB) with certain moieties known to those skilled in the art as 'prodrug moieties' as described, for example, in *Design of Prodrugs* by H. Bundgaard (Elsevier, 1985). Such examples could be a prodrug of a carboxyl group (such as —CO—O—CH$_2$—O—

CO-tBu as used in the pivampicillin prodrug of ampicillin), an amide (—CO—NH—CH$_2$—NAlk$_2$) or an amidine (—C(=N—O—CH$_3$)—NH$_2$).

Also included within the scope of the invention are metabolites of compounds with which the invention is concerned, that is, compounds formed in vivo upon administration of the drug. Some examples of metabolites include (i) where the compound of formula I contains a methyl group, an hydroxymethyl derivative thereof (—CH$_3$→—CH$_2$OH):

(ii) where the compound of formula I contains an alkoxy group, an hydroxy derivative thereof (—OR→—OH);

(iii) where the compound of formula I contains a tertiary amino group, a secondary amino derivative thereof (—NR$^1$R$^2$→—NHR$^1$ or —NHR$^2$);

(iv) where the compound of formula I contains a secondary amino group, a primary derivative thereof (—NHR$^1$→—NH$_2$);

(v) where the compound of formula I contains a phenyl moiety, a phenol derivative thereof (-Ph→-PhOH); and (vi) where the compound of formula I contains an amide group, a carboxylic acid derivative thereof (—CONH$_2$→COOH).

Structural Aspects of Compounds of the Invention

In the compounds with which the invention is concerned:

W is =CH— or =N—, but currently it is preferred that W be =CH—;

R$_4$ and R$_5$ are optional substituents, such as methyl, —OCH$_3$, —CF$_3$, —OCF$_3$, ethyl, cyclopropyl, oxo, hydroxyl, —F, —Cl, —Br, cyano, acetyl, amino, methylamino, dimethylamino, acetylamino, carbamate, —CONH$_2$, nitro, —COON or —CH$_2$OH. Thus, one of R$_4$ and R$_5$ may be hydrogen while the other is selected from the foregoing group of substituents. Alternatively, R$_4$ and R$_5$ may each be independently selected from the foregoing group of substituents. Presently, it is preferred that R$_4$ and R$_5$ are each independently fluoro or chloro, or one of R$_4$ and R$_5$ is hydrogen while the other is fluoro or chloro.

In the radical R$_3$, p may be 0, and m and/or n may be 1. Alternatively, p may be 1, and Z$^1$ may be an optionally substituted carbocyclic or heteroaryl radical having 3 to 6 ring atoms or an optionally substituted bicyclic carbocyclic or heteroaryl radical having 5 to 10 ring atoms, which is linked to the -(Alk$^1$)$_m$- part of R$_3$ and to the -(Alk$^2$)$_n$-Q part of R$_3$ via ring carbon or nitrogen atoms. Examples of divalent radicals Z$^1$ in this embodiment include those selected from the following, in either orientation:

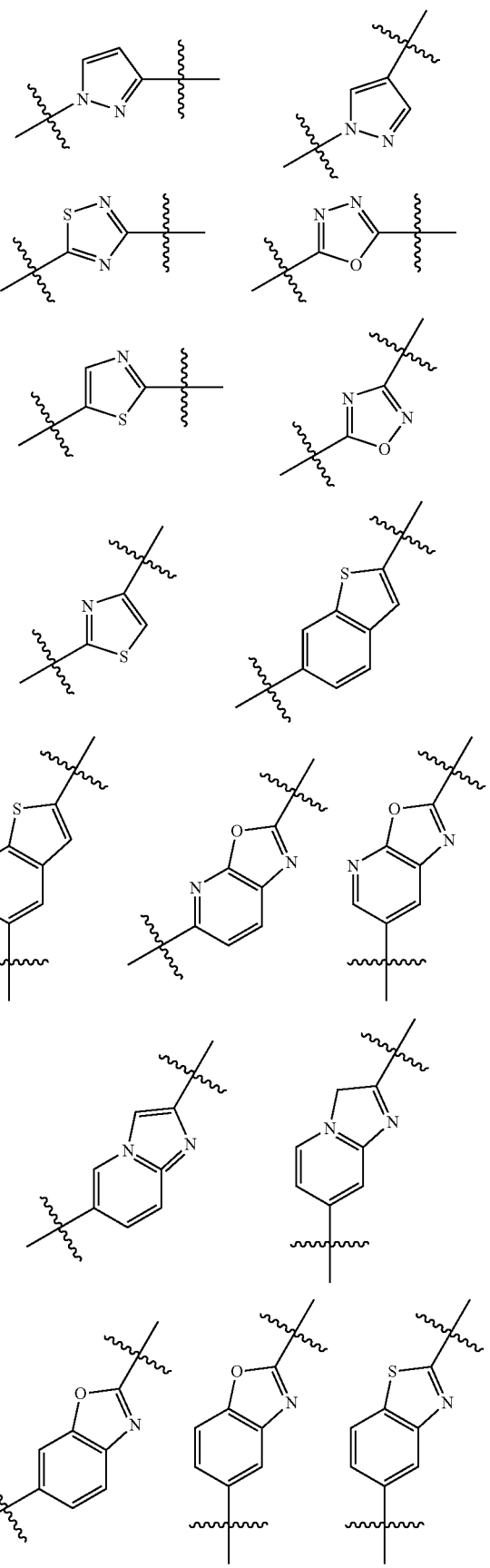

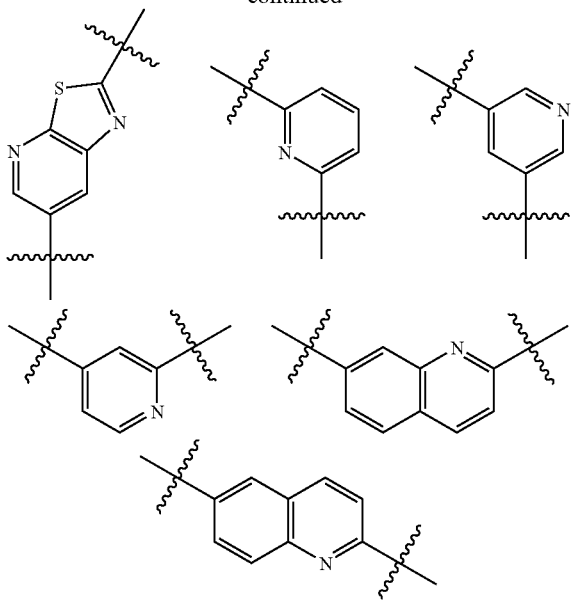

In the compounds with which the invention is concerned, and in any of the subclasses or embodiments of such compounds discussed above, Q may be hydrogen. However Q may also be a radical selected from any of the divalent $Z^1$ radicals specifically identified above but with one of the unsatisfied valencies thereof satisfied with hydrogen or an optional substituent.

In the compounds with which the invention is concerned, and in any of the subclasses or embodiments of such compounds discussed above n and/or m may be 0.

In all compounds and classes of compounds with which the invention is concerned, it is typical that the radical $R_3$, when fully extended, does not exceed the length of an unbranched saturated hydrocarbon chain of 14 carbon atoms, i.e. does not exceed about 16 Angstroms. For example, that length may be equivalent to that of an unbranched saturated hydrocarbon chain of from 6 to 12, or 9 to 12 carbon atoms, i.e. from about 6 to about 14, and from about 10 to about 14 Angstroms respectively.

In the compounds with which the invention is concerned, $Alk^1$ and $Alk^2$, when present, may be, for example, optionally substituted straight chain $C_1$-$C_6$ alkylene, $C_2$-$C_6$ alkenylene, or $C_2$-$C_6$ alkynylene radicals, each of which may optionally terminate with or be interrupted by —O—, —S—, —S(O)—, —S(O$_2$)—, —NH—, —N(CH$_3$)—, or —N(CH$_2$CH$_3$)—, —C(=O)—, —O—(C=O)—, —C(=O)—O—.

In some classes of compounds with which the invention is concerned $R_6$ and $R_7$ are each hydrogen.

In some classes of compound with which the invention is concerned $R_2$ is —OR$_8$, —OC(=O)R$_8$ or —SO$_2$R$_8$ wherein $R_8$ is optionally substituted $C_1$-$C_3$ alkyl or $C_2$-$C_3$ alkenyl, such as allyl. Optional substituents in $R_2$ include Cl, F, CN, OH, OCH$_3$, phenyl and phenoxy.

In other classes of compounds with which the invention is concerned, $R_2$ is —O-Alk$^4$-H, wherein Alk$^4$ is —(CH$_2$)$_a$— wherein a is 1, 2 or 3; or —CH$_2$(CH$_3$)—.

Specific examples of $R_2$ include hydrogen, —OH, —OCH$_3$, —OC(=O)CH$_3$ and —SO$_2$CH$_3$ Specific compounds with which the invention is concerned include those of the Examples herein.

Synthesis

There are multiple synthetic strategies for the synthesis of the compounds with which the invention is concerned, but all rely on known chemistry, known to the synthetic organic chemist. Thus, they can be synthesised according to procedures described in the standard literature and are well-known to the one skilled in the art. Typical literature sources are "Advanced Organic Chemistry", 4$^{th}$ Edition (Wiley), J March, "Comprehensive Organic Transformation", 2$^{nd}$ Edition (Wiley), R. C. Larock, "Handbook of Heterocyclic Chemistry", 2$^{rd}$ Edition (Pergamon), A. R. Katritzky), review articles such as found in "Synthesis", "Acc. Chem. Res.", "Chem. Rev", or primary literature sources identified by standard literature searches online or from secondary sources such as "Chemical Abstracts" or "Beilstein".

Typical routes to compounds with which the present invention is concerned are described in the Examples herein.

Pharmaceutical Utilities

As mentioned above, the compounds with which the invention is concerned are antibacterially active, since they inhibit bacterial growth. They are therefore of use in the treatment of bacterial infection in humans and non-human animals e.g. other mammals, birds and fish. The compounds include those which inhibit growth of Gram-positive organisms such as Bacillus subtilis and Staphylococcus aureus.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy. As is required in the pharmaceutical art, safe and permitted doses will be determined by clinical trial, but daily dosages can vary within wide limits and will be adjusted to the individual requirements in each particular case. Typically, however, the dosage adopted for each route of administration when a compound is administered alone to adult humans is 0.0001 to 150 mg/kg body weight. Such a dosage may be given, for example, from 1 to 5 times daily. For intravenous injection a suitable daily dose is from 0.0001 to 150 mg/kg body weight. A daily dosage can be administered as a single dosage or according to a divided dose schedule.

The compounds with which the invention is concerned may be prepared for administration by any route consistent with their pharmacokinetic properties, such as oral, topical, or sterile parenteral solutions or suspensions. The orally administrable compositions may be in the form of tablets, capsules, powders, granules, lozenges, liquid or gel preparations. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium, either subcutaneously, or intravenously, or intramuscularly, or intrasternally, or by infusion techniques, in the form of sterile injectable aqueous or oleaginous suspensions. Depending on the vehicle and concentration used, the drug can either be suspended or dissolved in the vehicle. Advantageously, adjuvants such as a local anaesthetic, preservative and buffering agents can be dissolved in the vehicle.

The antibacterial compounds of the present invention may be administered in combination with other antibacterial agents, especially those having mechanisms of action different from those of the present compounds. Compounds having activities other than antibacterial may also be administered with the compounds of the invention, for example anti-inflammatory or antipyretic compounds.

Since the compounds with which the invention is concerned are antibacterially active and inhibit bacterial growth, they are also of use in treating bacterial contamination of a substrate, such as hospital instruments or work surfaces. In order to treat a contaminated substrate, the compounds may be applied to the site of such contamination in an amount sufficient to inhibit bacterial growth.

The following examples illustrate the synthesis of compounds with which the invention is concerned.

Scheme 1:

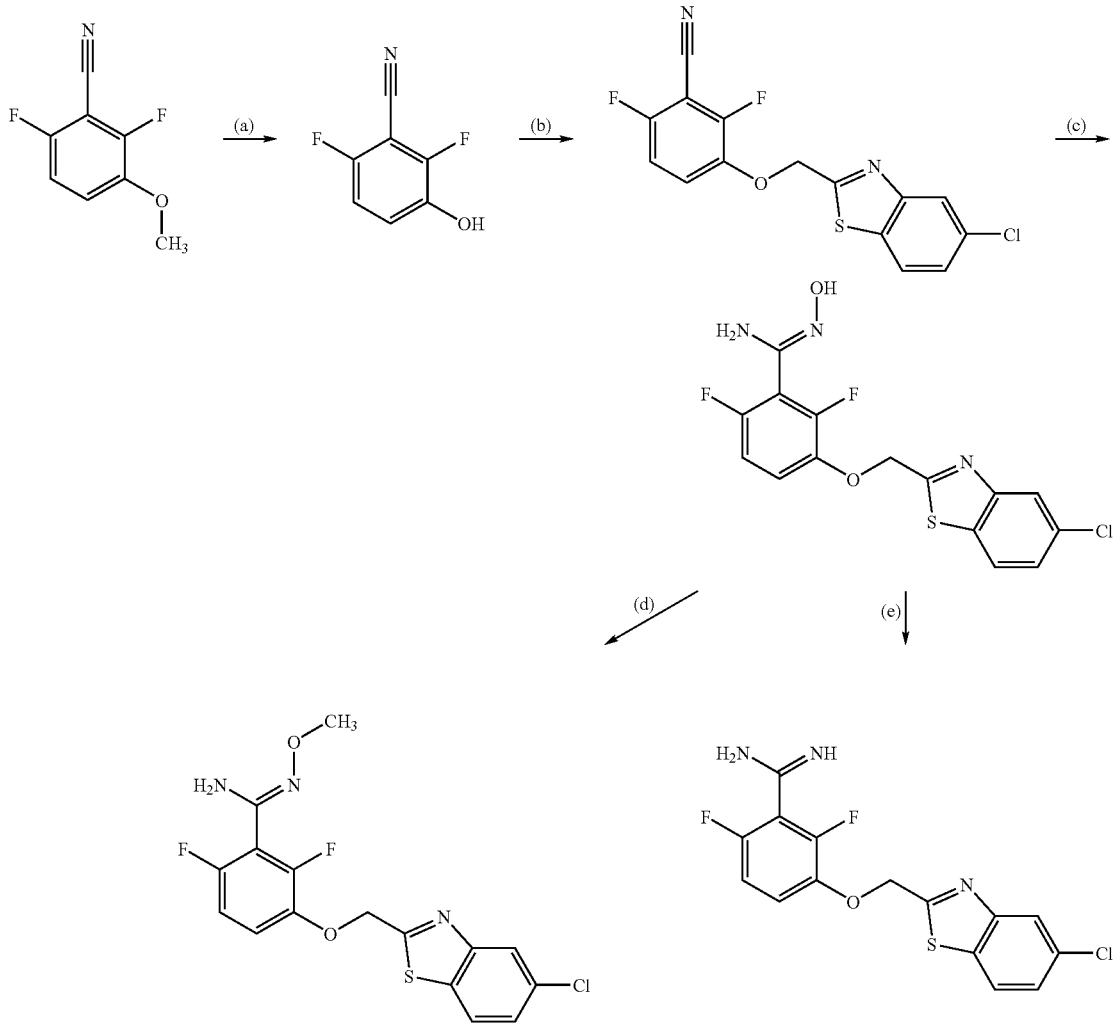

(a) BBr$_3$, CH$_2$Cl$_2$, room temperature; (b) 5-chloro-2-(chloromethyl)-1,3-benzothiazole, K$_2$CO$_3$, NaI, DMF, 60° C.; (c) NH$_2$OH·HCl, Na$_2$CO$_3$, abs. EtOH, 70° C.;

2,6-Difluoro-3-hydroxybenzenecarbonitrile

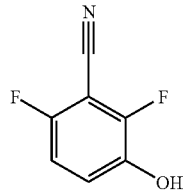

Synthesised from commercially available 2,6-difluoro-3-methoxybenzenecarbonitrile. Boron tribromide solution (1.0 M in $CH_2Cl_2$, 118.3 ml, 118.3 mmol, 2 equiv.) was added slowly, dropwise to stirred solution of 2,6-difluoro-3-methoxybenzenecarbonitrile (10 g, 59.1 mmol, 1 equiv.) in $CH_2Cl_2$ (270 ml), at room temperature The reaction mixture was stirred at room temperature for 5 days. The reaction mixture was poured into water (600 ml), separated and extracted with $CH_2Cl_2$ (200 ml×2). The extracts were washed with water (250 ml×3) and dried ($Na_2SO_4$) to give a buff solid (7.15 g). This was dissolved in dichloromethane (250 ml) and extracted with dilute aqueous NaOH (6 g in 250 ml of water× 2). The basic extracts were washed with $CH_2Cl_2$ (100 ml×3) and then acidified to pH 2 using concentrated HCl, extracted with $CH_2Cl_2$ (150 ml×4), washed with water (100 ml×2) and dried ($Na_2SO_4$) to give the desired compound as a cream solid (5.05 g). Yield 55%, mp 119-121° C., HPLC (Gemini C18, 50×4.6 mm): m/z 154 [M−H]−, Rt=3.07 min.

5-chloro-2-(chloromethyl)-1,3-benzothiazole

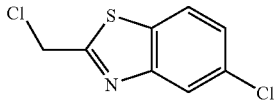 [SMILES: ClCc1nc2cc(Cl)ccc2s1]

4-chloro-2-amino-benzothiol (5 g, 31.3 mmol, 1 equiv.) was mixed with 2-chloro-1,1,1-trimethoxyethane (50.6 ml, 37.56 mmol, 1.2 equiv.) and heated at 60° C. with stirring for 1 hour (After 2 min the reaction mixture turned solid so more 2-chloro-1,1,1-trimethoxyethane (1.5 ml) was added). $Et_2O$ and pentane were added, however no precipitation occurred so the mixture was evaporated to dryness to give an orange solid. This was triturated by stirring with $Et_2O$ at room temperature The undissolved solid was filtered, rinsed with $Et_2O$ and pentane to give 1.5 g (22%) of light brown solid. The mother liquor was evaporated to dryness, dissolved in $Et_2O$, washed with 1 N HCl, $H_2O$, 10% $NaHCO_3$, $H_2O$ and brine. This was then dried ($MgSO_4$) and evaporated to a smaller volume when solid precipitated it was filtered and washed with pentane to give 2.18 g (32%) of light brown solid. The new mother liquor was treated as above to give a further 550 mg (8%) of product. Total yield 40%.

3-[(5-Chloro-1,3-benzothiazol-2-yl)methoxy]-2,6-difluorobenzenecarbonitrile

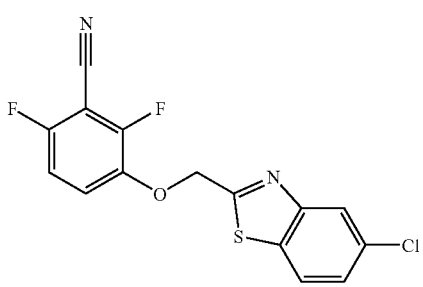 [SMILES: N#Cc1c(F)ccc(OCc2nc3cc(Cl)ccc3s2)c1F]

A mixture of 2,6-difluoro-3-hydroxybenzenecarbonitrile (4.5 g, 29.0 mmol), $K_2CO_3$ (6.01 g, 43.5 mmol) and NaI (0.78 g 5.8 mmol) in DMF (75 ml) was stirred at room temperature for 5 minutes. 5-chloro-2-(chloromethyl)-1,3-benzothiazole was then added and the mixture heated at 40° C. for 18 hours, cooled to room temperature and poured into water (450 ml). Buff solid was filtered off and dried (9.46 g). This was the recrystallised from acetonitrile (30 ml) and dried in vacuo at 40° C. to give a beige solid. Yield 79%, mp 145-147° C., HPLC (Gemini C18, 50×4.6 mm): m/z 337 [M+H]+, Rt=4.93 min.

Example 1

3-[(5-Chloro-1,3-benzothiazol-2-yl)methoxy]-2,6-difluoro-N'-hydroxybenzenecarboximidamide

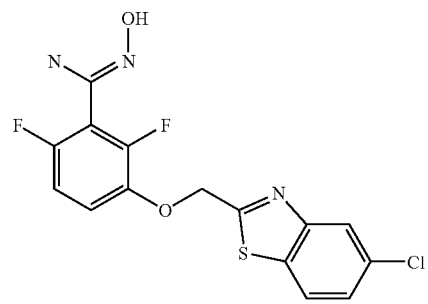 [SMILES: N/C(=N\O)c1c(F)ccc(OCc2nc3cc(Cl)ccc3s2)c1F]

A mixture of 3-[(5-chloro-1,3-benzothiazol-2-yl)methoxy]-2,6-difluorobenzene-carbonitrile (250 mg, 0.74 mmol, 1 equiv.), $Na_2CO_3$ (181 mg, 1.70 mmol, 2.3 equiv.) and hydroxylamine hydrochloride (103 mg, 1.48 mmol, 2 equiv.) in absolute EtOH (5 ml) was stirred at 70° C. for 8 h. Excess $Na_2CO_3$ (181 mg, 1.70 mmol, 2.3 equiv.) and hydroxylamine hydrochloride (103 mg, 1.48 mmol, 2 equiv.) were added and the heating continued for 1 h. The reaction mixture cooled at room temperature, diluted with water (40 ml) and extracted with $CH_2Cl_2$ (3×60 ml). The combined organic extracts were dried ($MgSO_4$) and evaporated to dryness under reduced pressure, to give 201 mg (73% yield) of the desired product. Mp 169-170° C., HPLC (Gemini C18, 50×4.6 mm): m/z 370 [M+H]+, Rt=3.82 min.

Example 2

3-[(5-Chloro-1,3-benzothiazol-2-yl)methoxy]-2,6-difluoro-N'-methoxybenzenecarboximidamide

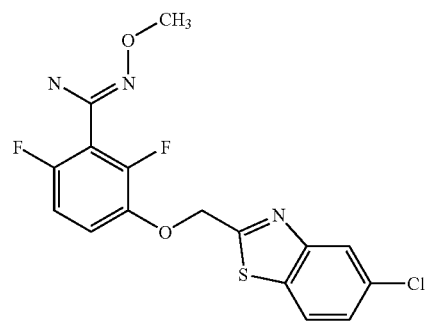 [SMILES: CO/N=C(\N)c1c(F)ccc(OCc2nc3cc(Cl)ccc3s2)c1F]

A mixture of 3-[(5-chloro-1,3-benzothiazol-2-yl)methoxy]-2,6-difluoro-N'-hydroxybenzenecarboximidamide (222, mg, 0.6 mmol, 1 equiv.), 0.7 N NaOH solution (0.97 ml, 0.68 mmol, 1.13 equiv.) and dimethylsulfate (0.60 ml, 0.63 mmol, 1.05 equiv.) in THF (4 ml) was stirred at 0° C. for 6 h. The mixture was poured into $H_2O$ (40 ml) and the precipitant solid was filtered and washed with $H_2O$ (2×10 ml) and $Et_2O$ (2×10 ml) to give 43 mg (yield 19%) of the desired product. Purity 70% by HPLC (Gemini C18, 50×4.6 mm): m/z 384 [M+H]$^+$, Rt=3.26 min. HPLC-MS analysis suggested also that there was 23% un-reacted starting material and 6% of the N-methylated by-product: 3-[(5-chloro-1,3-benzothiazol-2-yl)methoxy]-2,6-difluoro-N'-hydroxy-N-methylbenzenecarboximidamide.

Example 3

3-[(5-Chloro-1,3-benzothiazol-2-yl)methoxy]-2,6-difluorobenzenecarboximidamide

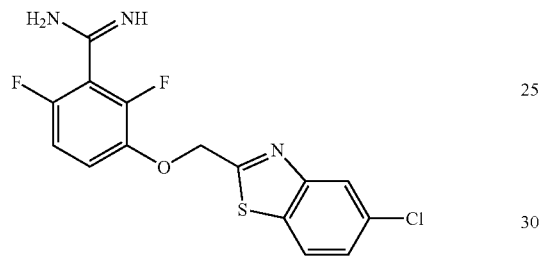

A mixture of 3-[(5-chloro-1,3-benzothiazol-2-yl)methoxy]-2,6-difluoro-N'-hydroxybenzenecarboximidamide (156, mg, 0.42 mmol, 1 equiv.), 10% Pd/C (63 mg) and ammonium formate (133 mg, 2.1 mmol, 5 equiv.) in glacial acetic acid (2 ml) was stirred under reflux for 3 h. The mixture was filtered through a pad of celite, alkalised to pH 10 with 0.5N NaOH and extracted with EtOAc (3×15 ml). The combined organic extracts were dried (MgSO$_4$) and evaporated to dryness under reduced pressure. The crude residue was dissolved in DMSO and precipitated by addition of $H_2O$. The solid was filtered, washed with $H_2O$ and pentane, to give 49 mg (33% yield). Purity 62% by HPLC (Gemini C18, 50×4.6 mm): m/z 354 [M+H]$^+$, Rt=3.09 min. HPLC-MS analysis suggested that there was also 6% un-reacted starting material and 21% of the title compound without the Cl atom.

Scheme 2:

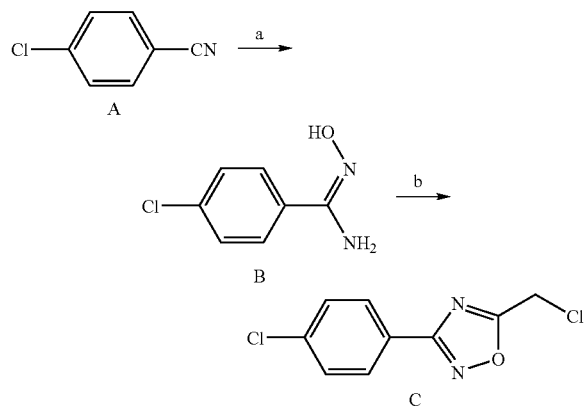

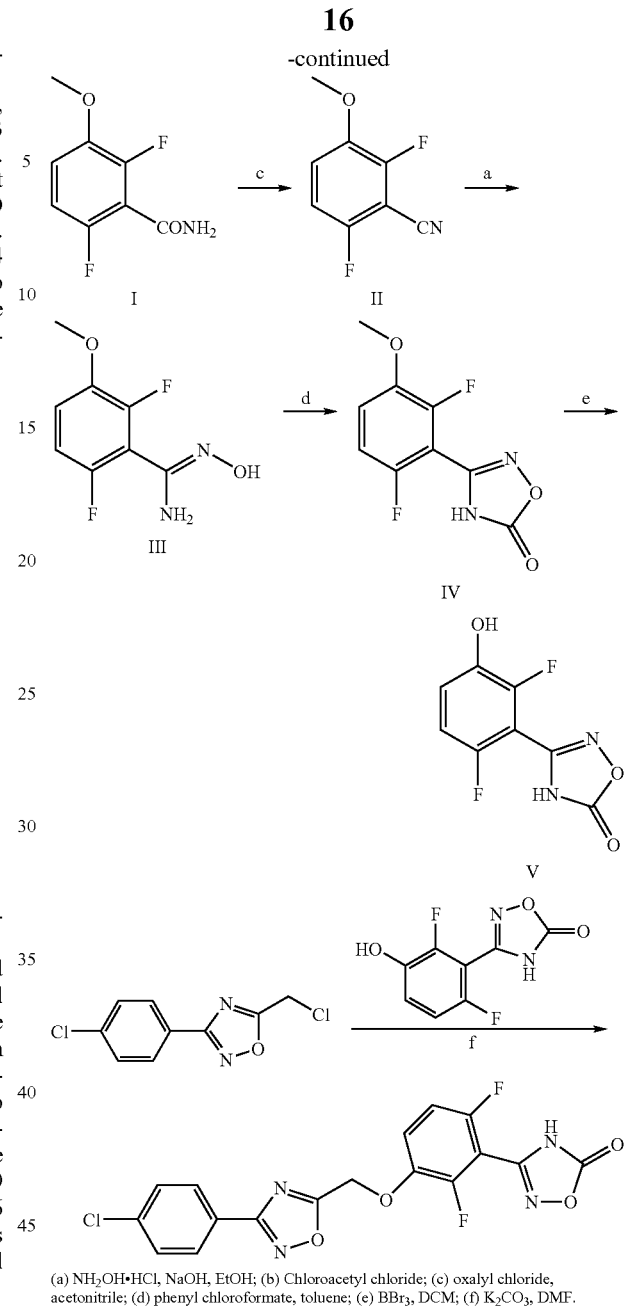

(a) NH$_2$OH·HCl, NaOH, EtOH; (b) Chloroacetyl chloride; (c) oxalyl chloride, acetonitrile; (d) phenyl chloroformate, toluene; (e) BBr$_3$, DCM; (f) K$_2$CO$_3$, DMF.

4-Chloro-N-hydroxybenzamide

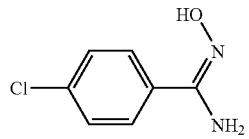

To a solution of 4-chlorobenzonitrile (0.50 g, 3.60 mmol) in EtOH (10 ml) was added hydroxylamine hydrochloride (0.15 g, 3.60 mmol) and NaOH (2.90 g, 3.60 mmol). The resulting reaction mixture was refluxed for 2 h. After the completion of the reaction (TLC monitoring), the mixture was concentrated, added EtOH and filtered. The filtrate was evaporated in vacuo and used as such for the next step (crude yield 0.50 g, 77%).

5-Chloromethyl-3-(4-chloro-phenyl)-[1,2,4]oxadiazole

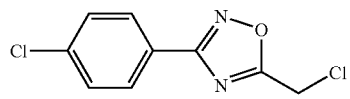

Chloroacetyl Chloride (5.0 ml) was added to a mixture of 4-chloro-N-hydroxybenzamide (0.40 g, 2.35 mmol) and K$_2$CO$_3$ (1.13 g, 8.2 mmol). The reaction mixture was heated at 100° C. for 15 min. After the completion of the reaction mixture (TLC monitoring), water (100 ml) was added and extracted with ethyl acetate (3×50 ml). The combined organics was washed with water, brine, dried (Na$_2$SO$_4$), filtered and concentrated. The crude residue was purified over silica gel (60-120 M, 1% EtOAc-Hexane) to get the desired product (0.13 g, 24%) as a white solid.

$^1$H NMR (CDCl$_3$, 400 MHz): δ 4.74 (s, 2H), 7.46 (d, J=8.0 Hz, 2H) and 8.02 (d, J=8.0 Hz, 2H).

2,6-Difluoro-3-methoxybenzonitrile

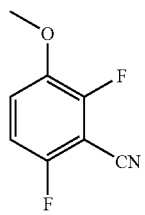

To an ice cold solution of DMF (0.45 ml) and acetonitrile (10 ml) was added oxalyl chloride (0.41 g, 0.28 ml, 3.20 mmol) dropwise while maintaining the temperature to 0° C. The reaction mixture was stirred at 0° C. for 40 min followed by addition of a solution of 2,6-difluoro-3-methoxybenzamide (0.50 g, 2.70 mmol) in DMF (4.5 ml). The resulting reaction mixture was stirred at 0° C. 40 min and then allowed to come to room temperature. After completion of reaction (10 min, TLC monitoring), triethyl amine (0.57 g, 0.80 ml, 5.67 mmol) was added dropwise. The reaction mass was concentrated in vacuo followed by addition of water (100 ml) and extraction with ethyl acetate (3×100 ml). The combined organics was washed with water, brine, dried (Na$_2$SO$_4$), filtered and concentrated. The crude residue was purified over silica gel (60-120 M, 10% EtOAc-Hexane) to get the desired product (0.30 g, 66%) as a white solid.

$^1$H NMR (DMSO-d$_6$, 400 MHz): δ 3.89 (s, 3H), 7.38 (m, 1H) and 7.66 (m, 1H).

2,6-Difluoro-N-hydroxy-3-methoxybenzamidine

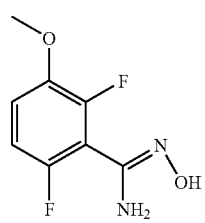

To a solution of 2,6-difluoro-3-methoxybenzonitrile (0.30 g, 1.70 mmol) in EtOH (10 ml) was added hydroxylamine hydrochloride (0.12 g, 1.70 mmol) and NaOH (0.071 g, 1.70 mmol). The resulting reaction mixture was refluxed for 15 h. After the completion of the reaction (TLC monitoring), the mixture was concentrated, added EtOH and filtered. The filtrate was evaporated in vacuo and the crude residue was purified over silica gel (60-120 M, 30% EtOAc-Hexane) to get the desired product (0.15 g, 42%) as a white solid.

$^1$H NMR (DMSO-d$_6$, 400 MHz): δ 3.83 (s, 3H), 5.95 (br s, 2H), 7.08 (m, 1H), 7.23 (m, 1H) and 9.56 (br s, 1 H).

3-(2,6-Difluoro-3-methoxyphenyl)-4H-[1,2,4]oxadiazol-5-one

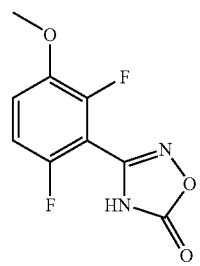 [SMILES: COc1ccc(F)c(-c2noc(=O)[nH]2)c1F]

To an ice cold solution of 2,6-difluoro-N-hydroxy-3-methoxybenzamidine in DCM (5 ml) was added triethyl amine (0.07 g, 0.11 ml, 0.77 mmol) followed by dropwise addition of phenyl chloroformate. The resulting reaction mixture was stirred at room temperature for 1 h. After the completion of the reaction (TLC monitoring), the organic layer was washed with water until the DCM layer was neutral. The organic layer was dried (Na$_2$SO$_4$), filtered and concentrated to get a white solid. The solid compound was then dissolved in toluene (2 ml) and refluxed it at 100° C. for 2 h. After the completion of the reaction (TLC monitoring), water (100 ml) was added and extracted with ethyl acetate (3×100 ml). The combined organics was washed with water, brine, dried (Na$_2$SO$_4$), filtered and concentrated. The crude residue was purified over silica gel (60-120 M, 35% EtOAc-Hexane) to get the desired product (0.09 g, 80%) as a white solid. MS ES+ (229.18).

3-(2,6-Difluoro-3-hydroxyphenyl)-4H-[1,2,4]oxadiazol-5-one

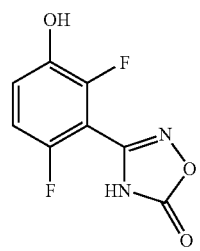 [SMILES: O=c1[nH]c(-c2c(F)ccc(O)c2F)no1]

A solution of 3-(2,6-difluoro-3-methoxyphenyl)-4H-[1,2,4]oxadiazol-5-one (0.09 g, 0.39 mmol) in DCM (3 ml) was cooled to −78° C. followed by addition of BBr$_3$ (0.10 ml, 1.18 mmol). The reaction mixture was stirred at 25° C. for 2 h. After the completion of the reaction mixture (TLC monitoring), solution of NaHCO$_3$ (20 ml) was added at 0° C. and extracted with ethyl acetate (3×50 ml). The combined organics was washed with water, brine, dried (Na$_2$SO$_4$), filtered and concentrated. The crude residue was purified by column chromatography on silica (60-120 M) using ethyl acetate/hexane (50:50) as the eluent to provide the title compound as white solid (0.08 g, 95%).

Example 4

3-{3-[3-(4-Chloro-phenyl)-[1,2,4]oxadiazol-5-yl-methoxy]-2,6-difluorophenyl}-4H-[1,2,4]oxadiazol-5-one

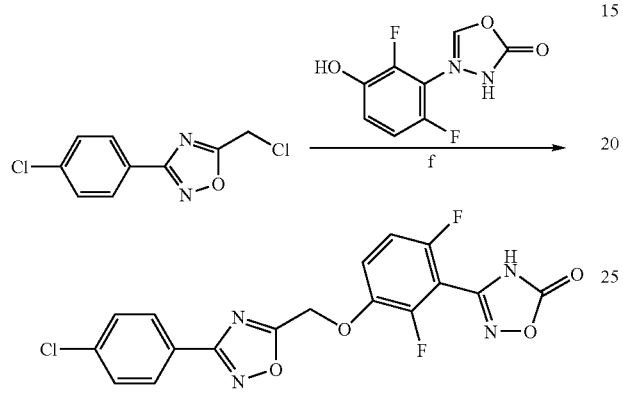

To a solution of 5-chloromethyl-3-(4-chlorophenyl)-[1,2,4]oxadiazole (0.080 g, 0.35 mmol) in anhydrous DMF (2 ml) was added 3-(2,6-difluoro-3-hydroxyphenyl)-4H-[1,2,4]oxadiazol-5-one (0.075 g, 0.35 mmol) and potassium carbonate (0.17 g, 1.22 mmol) was added. The reaction mixture was stirred at 25° C. for 24 h under nitrogen atmosphere. After the completion of the reaction (TLC monitoring), the reaction mixture was evaporated to dryness under reduced pressure, added water and extracted with EtOAc (3×50 ml). The combined organics was washed with water, dried (Na$_2$SO$_4$), filtered and concentrated. The crude residue was purified over silica (60-120 M) using ethyl acetate/hexane (45:55) as the eluent to provide the title compound as off white solid (0.0088 g, 6%).

$^1$H NMR (DMSO-d$_6$, 400 MHz): δ 5.77 (s, 2H), 7.38 (m, 1H), 7.67 (d, J=8.40 Hz, 2H), 7.70 (m, 1 H) and 8.03 (d, J=8.40 Hz, 2H).

HPLC (Xbridge C-18, 250×4.6 mm; 246 nm) Rt=16.54 min, 87%.

Scheme 3:

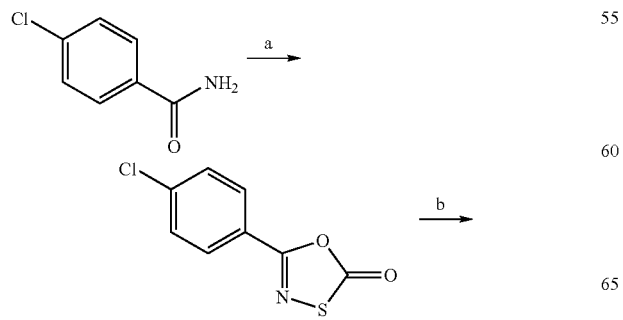

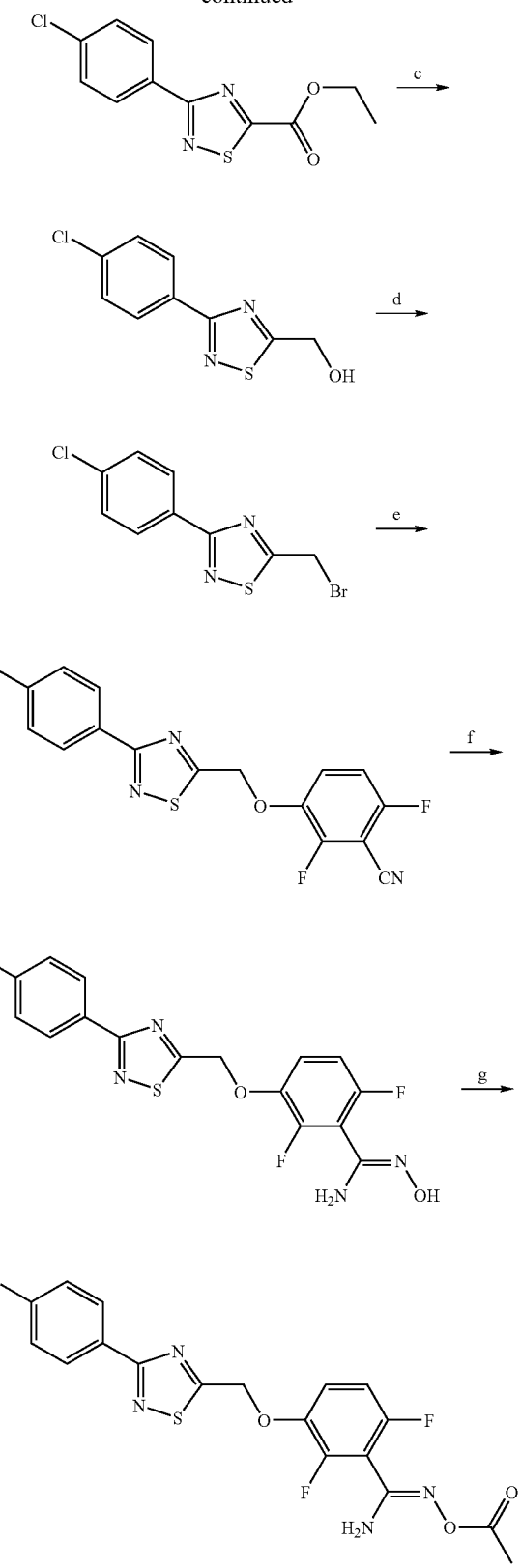

(a) Chlorocarbonylsulfenyl chloride, toluene, 80° C., 3 h; (b) Ethyl cyanoformate, 1,2-dichlorobenzene, 150° C., 24 h; (c) NaBH$_4$, EtOH, 2 h; (d) PBr$_3$, toluene, 120° C.; (e) 2,6-difluoro-3-hydroxybenzonitrile, K$_2$CO$_3$, DMF; (f) NH$_2$OH•HCl, NaOH, ethanol, water, 75° C.; (g) acetyl chloride, di-isopropylethylamine, DCM, 0° C., 1 h.

5-(4-Chlorophenyl)-[1,3,4]oxathiazol-2-one

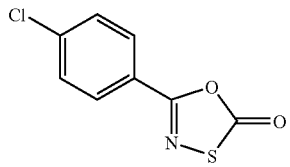 [SMILES: O=c1oc(-c2ccc(Cl)cc2)ns1]

To a solution of 4-chlorobenzamide (1.0 g, 6.42 mmol) in toluene (25 ml) was added chlorocarbonylsulfenyl chloride (1.0 ml, 12.85 mmol). The resulting reaction mixture was refluxed at 80° C. for 3 h. After the completion of the reaction (TLC monitoring), the mixture was concentrated, added diethyl ether and washed twice with water, twice with 5% NaHCO$_3$, again with water, and was dried (Na$_2$SO$_4$), concentrated under vacuum to give the product (crude yield 1.37 g, 100%) that was carried forward to the next step without further purification.

3-(4-Chlorophenyl)-[1,2,4]thiadiazole-5-carboxylic acid ethyl ester

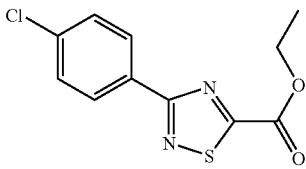 [SMILES: CCOC(=O)c1nc(-c2ccc(Cl)cc2)ns1]

To a solution of 5-(4-chlorophenyl)-[1,3,4]oxathiazol-2-one (1.35 g, 6.32 mmol) in 1,2-dichlorobenzene (5 ml) was added ethyl cyanoformate (2.50 ml, 25.27 mmol). The resulting reaction mixture was refluxed for 24 h at 150° C. After the completion of the reaction (TLC monitoring), added ice-cold water and extracted with ethyl acetate (3×100 ml). The combined organic layer was dried over Na$_2$SO$_4$, filtered and concentrated under vacuum, to get the desired product (1.44 g, 85%).

[3-(4-Chlorophenyl)-[1,2,4]thiadiazol-5-yl]-methanol

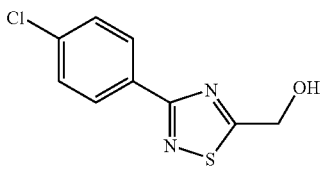 [SMILES: OCc1nc(-c2ccc(Cl)cc2)ns1]

To a solution of 3-(4-chlorophenyl)-[1,2,4]thiadiazole-5-carboxylic acid ethyl ester (0.85 g, 3.16 mmol) in EtOH (30 ml) was added sodium borohydride (0.30 g, 7.90 mmol) portion wise. The resulting reaction mixture was stirred at room temperature for 2 h. After the completion of the reaction (TLC monitoring), the reaction mass was cooled to 0° C., quenched it with 10 ml of water and concentrated under vacuum. Added 100 ml water and extracted with ethyl acetate (3×50 ml). The combined organic layer was dried over Na$_2$SO$_4$, filtered and concentrated under vacuum. The crude residue was purified over silica gel (100-200 M, 20% EtOAc-Hexane) to get the desired product (0.53 g, 74%).

5-Bromomethyl-3-(4-chlorophenyl)-[1,2,4]thiadiazole

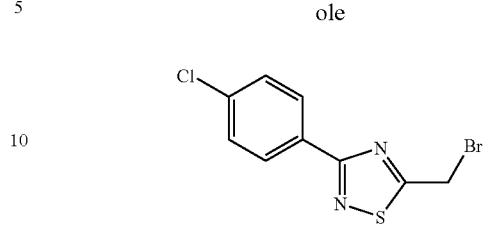

To a solution of [3-(4-chlorophenyl)-[1,2,4]thiadiazol-5-yl]-methanol (0.25 g, 1.10 mmol) in toluene (8 ml) was added PBr$_3$ (0.17 ml, 1.65 mmol). The resulting reaction mixture was refluxed at 120° C. for 15 min. After the completion of the reaction (TLC monitoring), the reaction mixture was cooled to 0° C., added water (50 ml) and extracted with ethyl acetate (3×50 ml). The combined organics was washed with saturated NaHCO$_3$ solution, dried over Na$_2$SO$_4$, filtered and concentrated under vacuum. The crude residue was purified over silica gel (100-200 M, 2% EtOAc-Hexane) to get the desired product (0.24 g, 75%).

3-[3-(4-Chlorophenyl)-[1,2,4]thiadiazol-5-yl-methoxy]-2,6-difluorobenzonitrile

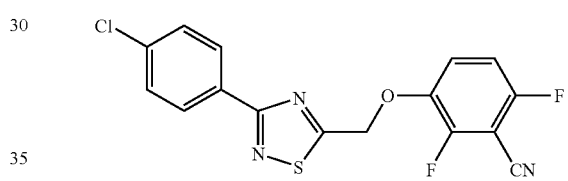

To a solution of 5-bromomethyl-3-(4-chlorophenyl)-[1,2,4]thiadiazole (0.24 g, 0.82 mmol) in DMF (7 ml) was added 2,6-difluoro-3-hydroxybenzonitrile (0.12 g, 0.74 mmol) and potassium carbonate (0.39 g, 2.90 mmol). The reaction mixture was stirred at 25° C. for 2 h under nitrogen atmosphere. After the completion of the reaction (TLC monitoring), the reaction mixture was evaporated to dryness under vacuum, added 50 ml water and extracted with ethyl acetate (3×40 ml). The combined organic layer was dried over Na$_2$SO$_4$, filtered and concentrated under vacuum. The crude residue was purified over silica gel (100-200 M, 15% EtOAc-Hexane) to get the desired product (0.30 g, 73%).
$^1$H NMR (DMSO-d$_6$, 400 MHz): δ 5.88 (s, 2H), 7.45 (m, 1H), 8.80 Hz, 2H), 7.85 (m, 1H) and 8.23 (d, J=8.80 Hz, 2H).

Example 5

3-[3-(4-Chlorophenyl)-[1,2,4]thiadiazol-5-yl-methoxy]-2,6-difluoro-N-hydroxybenzamidine

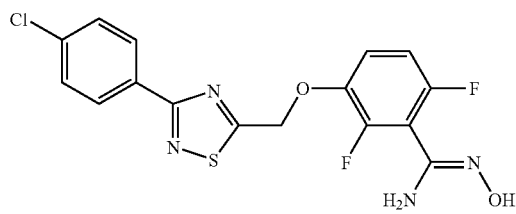 [SMILES: N/C(=N\O)c1c(F)ccc(OCc2nc(-c3ccc(Cl)cc3)ns2)c1F]

To a solution of 3-[3-(4-chlorophenyl)-[1,2,4]thiadiazol-5-ylmethoxy]-2,6-difluorobenzonitrile (0.10 g, 2.75 mmol) in EtOH (3 ml) was added hydroxylamine hydrochloride (0.48 g, 6.87 mmol) and NaOH (0.27 g, 6.87 mmol). The resulting reaction mixture was refluxed overnight. After the completion of the reaction (TLC monitoring), the mixture was concentrated, added EtOH and filtered. The filtrate was evaporated in vacuum to get the desired product (0.75 g, 69%).

¹H NMR (DMSO-d₆, 400 MHz): δ 5.82 (s, 2H), 6.01 (br s, 2H), 7.13 (m, 1H), 7.46 (m, 1H), 7.64 (m, 2H), 8.24 (m, 2H), 9.63 (br s, 1 H). MS ES+ (397.07).

HPLC (Acquity BEH C-18, 100×2.1 mm) Rt=6.07 min, 86%.

Example 6

3-[3-(4-Chlorophenyl)-[1,2,4]thiadiazol-5-yl-methoxy]-2,6-difluoro-N-acylbenzamidine

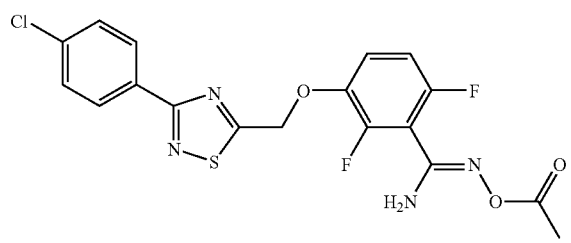 [SMILES: CC(=O)O/N=C(\N)c1c(F)ccc(OCc2nc(-c3ccc(Cl)cc3)ns2)c1F]

To a solution of 3-[3-(4-chlorophenyl)-[1,2,4]thiadiazol-5-ylmethoxy]-2,6-difluoro-N-hydroxybenzamidine (0.025 g, 0.06 mmol) in DCM (5.0 ml) was added diisopropylethylamine (0.022 g, 0.13 mmol) and acetyl chloride (0.006 g, 0.08 mmol). The reaction mixture was stirred at 0° C. for 1 h and then at 25° C. for 8 h under nitrogen atmosphere. After the completion of the reaction (TLC monitoring), added 30 ml ethyl acetate and washed by water (20 ml). The organic layer was dried over Na₂SO₄, filtered and concentrated under vacuum. The crude residue was purified through prep-HPLC to get the desired compound (0.011 g, 39%).

¹H NMR (DMSO-d₆, 400 MHz): δ 2.11 (s, 3H), 5.82 (s, 2H), 7.14 (br s, 2H), 7.23 (m, 1H), 7.53 (m, 1H), 7.64 (d, J=8.40 Hz, 2H) and 8.24 (d, J=8.40 Hz, 2H). MS ES+ (439.17).

HPLC (Acquity BEH C-18, 100×2.1 mm) Rt=6.34 min, 99%.

Scheme-4:

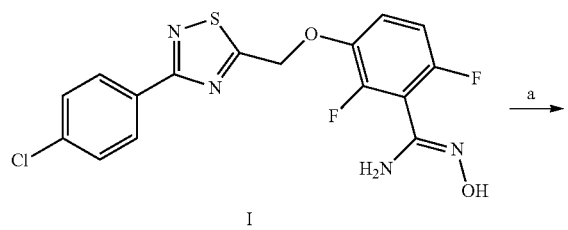

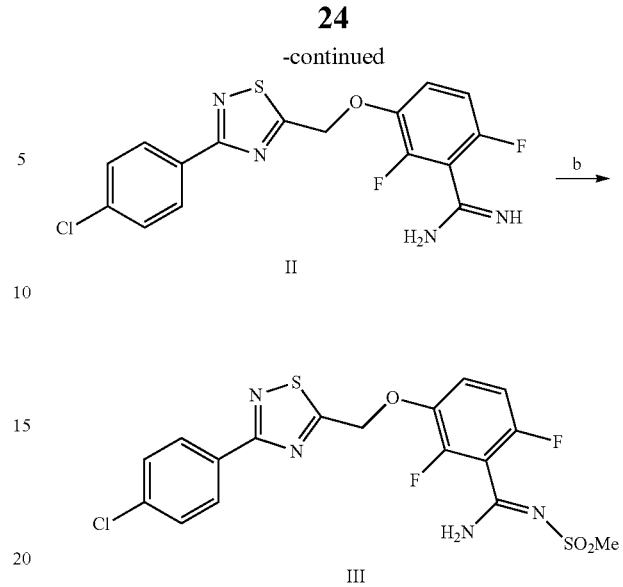

(a) (i) Ac2O, AcOH, THF; (ii) H2, Pd—C; (b) KOtBu, MsCl, THF.

The preparation of int I (Example 5) is described in scheme 3.

Example 7

3-((3-(4-chlorophenyl)-1,2,4-thiadiazol-5-yl)methoxy)-2,6-difluorobenzimidamide (II)

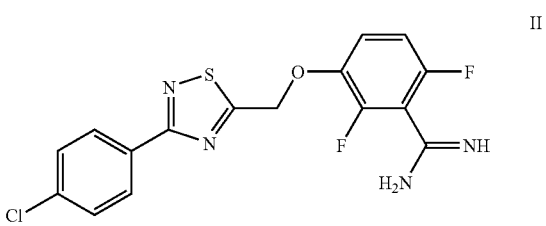 [SMILES: N=C(N)c1c(F)ccc(OCc2nc(-c3ccc(Cl)cc3)ns2)c1F]

To a solution of 3-((3-(4-chlorophenyl)-1,2,4-thiadiazol-5-yl)methoxy)-2,6-difluoro-N'-hydroxybenzimidamide (0.02 g, 0.05 mmol) in AcOH (0.50 ml) was added acetic anhydride (6 μL, 0.06 mmol) followed by addition of THF (1.0 ml) under nitrogen atmosphere. The resulting reaction mixture was stirred at room temperature for 1 h after which Pd-C (10%, 2.0 mg) was added and the resulting solution was stirred under hydrogen for 4 h. After the completion of the reaction (TLC monitoring), the reaction mass was filtered through celite bed, washed the celite bed with THF (3-4 times) and concentrated the filtrate. The residue was purified over neutral alumina (40% MeOH-DCM) to get the desired product (11 mg, 58%).

¹H-NMR (DMSO-d₆, 400 MHz): δ 5.90 (s, 2H), 7.39 (m, 1H), 7.65 (d, J=8.40 Hz, 2H), 7.73 (m, 1 H), 8.24 (d, J=8.40 Hz, 2H) and 9.60 (br s, 3H). MS: 381.02 (M+H)⁺.

HPLC (Acquity BEH C-18, 100×2.1 mm; 270 nm) Rt=5.49 min, 98.96%.

Example 8

3-((3-(4-chlorophenyl)-1,2,4-thiadiazol-5-Amethoxy)-2,6-difluoro-N'-(methylsulfon-yl)benzamidine

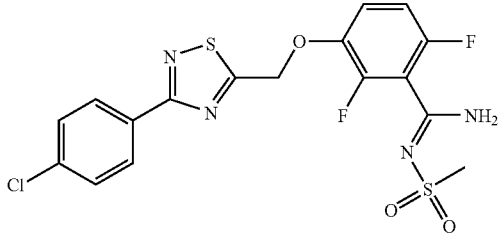

II

To a stirring solution of 3-((3-(4-chlorophenyl)-1,2,4-thiadiazol-5-yl)methoxy)-2,6-difluorobenz-amidine (0.05 g, 0.13 mmol) in dry THF were added KO$^t$Bu (0.03 g, 0.26 mmol) and MsCl (0.03 g, 0.26 mmol) at 0° C. The reaction mixture was slowly warmed to room temperature and stirred for 1 h. After completion of the reaction (TLC monitoring) the reaction mixture was diluted with EtOAc and washed with water. The organic layer was dried over Na$_2$SO$_4$, filtered and concentrated. The crude residue was purified over basic alumina (2% MeOH in DCM) to get the desired compound (0.04 g, 63%).

$^1$H-NMR (CDCl$_3$, 300 MHz): δ 3.10 (s, 3H), 5.56 (s, 2H), 5.95 (brs, 1H), 6.95 (m, 1H), 7.20 (m, 1H), 7.45 (d, J=8.4Hz, 2H) and 8.22 (d, J=8.4 Hz, 2H).

LCMS (Zorbax eclipse 0-18, 4.6×100 mm) Rt=6.03 min, 97%, [M+1]$^+$=459.18.

HPLC (Develosil ODS HG-5, 4.6×250 mm) Rt=9.47 min, 99%.

Scheme-5:

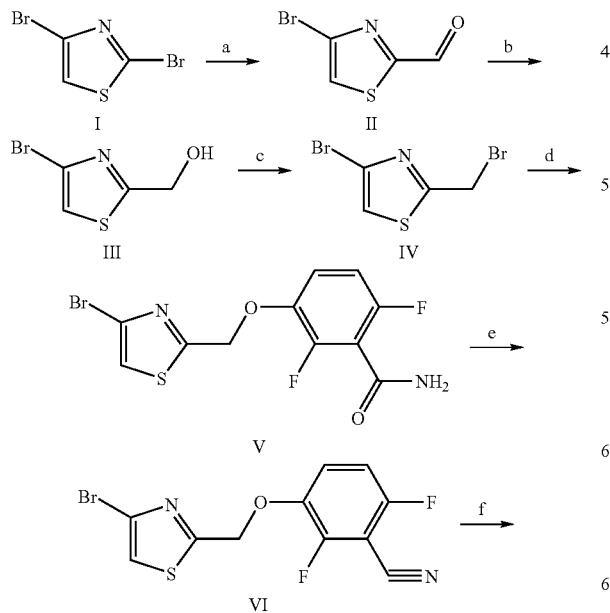

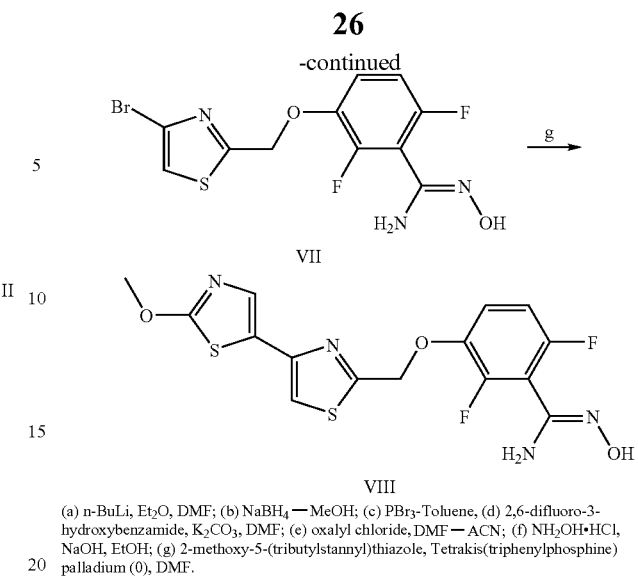

(a) n-BuLi, Et$_2$O, DMF; (b) NaBH$_4$—MeOH; (c) PBr$_3$-Toluene, (d) 2,6-difluoro-3-hydroxybenzamide, K$_2$CO$_3$, DMF; (e) oxalyl chloride, DMF—ACN; (f) NH$_2$OH•HCl, NaOH, EtOH; (g) 2-methoxy-5-(tributylstannyl)thiazole, Tetrakis(triphenylphosphine) palladium (0), DMF.

4-Bromothiazole-2-carbaldehyde (II)

To a solution of 2,4-dibromothiazole (2.50 g, 10.28 mmol) in diethyl ether (50 ml) cooled to −78° C. was added n-butyl lithium (1.40 M, 8.80 ml, 12.38 mmol) and the resulting reaction mixture was stirred for 15 min at the same temperature followed by addition of DMF (5.0 ml, 64.30 mmol). The reaction mass was then allowed to come to room temperature and stirred for 1 h. After the completion of the reaction (TLC monitoring), the reaction mass was cooled to 0° C. and quenched with saturated NH$_4$Cl solution (aqueous). Water was then added to the reaction mass and extracted with diethyl ether (3×100 ml). The combined organics was then dried over anhydrous Na$_2$SO$_4$, filtered and concentrated to get the desired product (2.10 g, quantitative crude yield) that was carried forward to the next step without further purification.

(4-Bromothiazol-2-yl)methanol (III)

To an ice-cold solution of 4-bromothiazole-2-carbaldehyde (1.78 g, 9.27 mmol, crude obtained above), in methanol (30 ml) was added NaBH$_4$ (1.76 g, 46.35 mmol) portion wise. The resulting reaction mixture was stirred at room temperature for 2 h. After completion of the reaction (TLC monitoring), the reaction mass was cooled to 0° C., quenched it with 25 ml of water and concentrated under vacuum. Added 50 ml water and extracted with EtOAc (3×100 ml). The combined organics was dried over anhydrous Na₂SO₄, filtered and concentrated under reduced pressure. The crude residue was purified over silica gel (60-120 M, 10% EtOAc-Hexane) to get the desired product (1.40 g, 78%). MS: 194.01 (M+H)⁺.

4-Bromo-2-(bromomethyl)thiazole (IV)

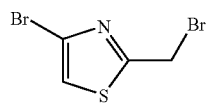

IV

To a solution of (4-bromothiazol-2-yl)methanol (2.0 g, 10.30 mmol) in toluene (20 ml) was added PBr₃ (1.49 ml, 15.46 mmol) and the resulting reaction mixture was heated at 110° C. for 2 h. After the completion of the reaction (TLC monitoring), the reaction mixture was cooled to 0° C., added water (50 ml) and extracted with EtOAc (3×100 ml). The combined organics was washed with saturated NaHCO₃ solution, dried over anhydrous Na₂SO₄, filtered and concentrated under reduced pressure to get the desired product (1.57 g) that was carried forward to the next step without further purification.

3((4-Bromothiazol-2-yl)methoxy)-2,6-difluorobenzamide (V)

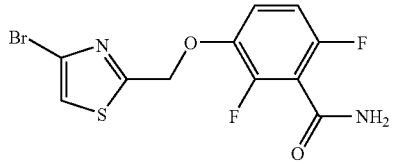

V

To a solution of 4-bromo-2-(bromomethyl)thiazole (1.57 g, 6.10 mmol) in DMF (15 ml) was added dried K₂CO₃ (2.95 g, 21.38 mmol) followed by addition of 2,6-difluoro-3-hydroxybenzamide (1.05 g, 6.10 mmol). The resulting reaction mass was stirred at room temperature for 2 h. After the completion of the reaction (TLC monitoring), ice-cold water was added (50 ml) followed by extraction with EtOAc (3×100 ml). The combined organics was washed with brine, dried (Na₂SO₄), filtered and concentrated. The residue was washed with ether and the solid thus obtained was filtered to get the desired product (1.56 g, 74%).

¹H NMR (DMSO-d₆, 400 MHz): δ 5.53 (s, 2H), 7.11 (m, 1H), 7.35 (m, 1H), 7.88 (br s, 1H), 7.92 (s, 1H) and 8.16 (br s, 1H).

3-((4-Bromothiazol-2-yl)methoxy)-2,6-difluorobenzonitrile (VI)

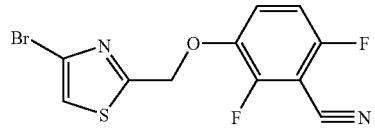

VI

To an ice cold solution of DMF (0.20 ml) and acetonotrile (5 ml) was added oxalyl chloride (45 μL, 0.52 mmol) dropwise while maintaining the temperature to 0° C. The reaction mixture was stirred at 0° C. for 40 min followed by addition of a solution of 3-((4-bromothiazol-2-yl)methoxy)-2,6-difluorobenzamide (0.15 g, 0.43 mmol) in DMF (2 ml). The resulting reaction mixture was stirred at 0° C. 40 min and then allowed to come to room temperature. After completion of reaction (10 min, TLC monitoring), triethyl amine (100 μL, 0.86 mmol) was added dropwise. The reaction mass was concentrated in vaccuo followed by addition of water (50 ml) and extraction with ethyl acetate (3×75 ml). The combined organics was washed with water, brine, dried (Na₂SO₄), filtered and concentrated. The crude residue was purified over silica gel (60-120 M, 20% EtOAc-Hexane) to get the desired product (0.10 g, 71%).

¹H NMR (DMSO-d₆, 400 MHz): δ 5.59 (s, 2H), 7.43 (m, 1H), 7.78 (m, 1H) and 7.94 (s, 1H),

3-((4-Bromothiazol-2-yl)methoxy)-2,6-difluoro-N'-hydroxy benzimidamide (VII)

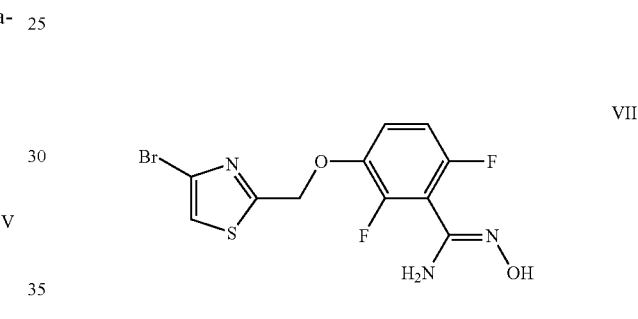

VII

To a solution of 3-((4-bromothiazol-2-yl)methoxy)-2,6-difluorobenzonitrile (0.10 g, 0.30 mmol) in EtOH (5 ml) was added hydroxylamine hydrochloride (0.103 g, 1.50 mmol) and NaOH (0.060 g, 1.50 mmol). The resulting reaction mixture was refluxed for 3 h. After the completion of the reaction (TLC monitoring), the mixture was concentrated, added EtOH and filtered. The filtrate was evaporated in vaccuo and used as such for the next step (crude yield 0.07 g, 63%). MS: 363.93 (M+H)⁺.

Example 9

2,6-difluoro-N'-hydroxy-3-((2'-methoxy-4,5'-bithiazol-2-yl)methoxy) benzimidamide (VIII)

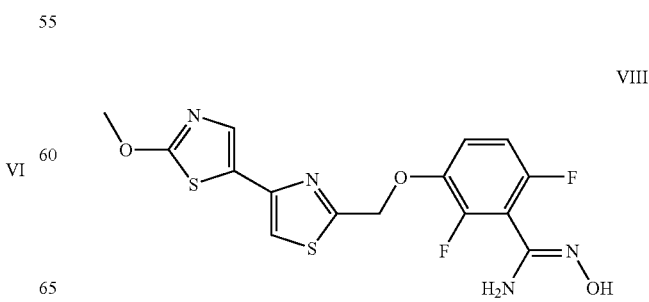

VIII

To a solution of 3-((4-bromothiazol-2-yl)methoxy)-2,6-difluoro-N'-hydroxy benzimidamide (0.20 g, 0.55 mmol) in DMF (4.0 ml) was added 2-methoxy-5-(tributylstannyl)thiazole (0.23 g, 0.55 mmol) and the resulting reaction mixture was purged with nitrogen for 15 min. Tetrakis(triphenylphosphine) palladium (0) (0.06 g, 0.05 mmol) was then added and the reaction mixture was heated at 100° C. for 3 h under the nitrogen atmosphere. The reaction mixture was then cooled to room temperature, added water (25 ml) and extracted with ethyl acetate (3×50 ml). The combined organic layers were dried over anhydrous $Na_2SO_4$, and evaporated to dryness under reduced pressure. The compound was purified by column chromatography on silica (60-120 M, 35% EtOAc-Hexane) yielding the title compound as white solid (0.06 g, 27%).

$^1$H NMR (DMSO-$d_6$, 400 MHz): δ 4.05 (s, 3H), 5.53 (s, 2H), 5.99 (br s, 2H), 7.10 (m, 1H), 7.37 (m, 1H), 7.68 (s, 1H), 7.98 (s, 1H) and 9.60 (s, 1H). MS: 399.0 $(M+H)^+$.

HPLC (Acquity BEH C-18, 100×2.1 mm; 278 nm) Rt=5.14 min, 92.23%.

Minimal Inhibitory Concentration (MIC) Testing

Compounds of this invention were tested for antimicrobial activity by susceptibility testing in liquid or on solid media. MICs for compounds against each strain were determined by the broth microdilution or agar dilution method according to the guidelines of the Clinical Laboratories and Standards Institute, formerly the National Committee for Clinical Laboratory Standards (Clinical Laboratories and Standards Institute. *Methods for Dilution Antimicrobial Susceptibility Tests for Bacteria That Grow Aerobically; Approved Standard—Seventh Edition*. Document M7-A7. CLSI, Wayne, Pa., 2006; Clinical Laboratories and Standards Institute.

Compounds of the current invention were found to have antimicrobial activity in the MIC assay described above.

Results

Table 1 shows the Minimal Inhibitory Concentration (MIC) of the Examples against the pathogenic organism *Staphylococcus aureus* ATCC29213. Activities were scored as 'A' if the MIC was less than or equal to 0.125 micrograms/ml, 'B' if the MIC was 0.25 to 4 micrograms/ml and 'C' if the MIC was greater than 4 micrograms/ml.

TABLE 1

| *Staphylococcus aureus* MICs | |
|---|---|
| Example | Activity |
| 1 | C |
| 2 | B |
| 3 | C |
| 4 | C |
| 5 | A |
| 6 | B |
| 7 | C |
| 8 | C |
| 9 | A |

The invention claimed is:
1. A compound of formula (IA)' or (IB), or a salt thereof:

(IA)

(IB)

wherein
W is =CH— or =N—;
$R_3$ is a radical selected from those of formulae A-J:

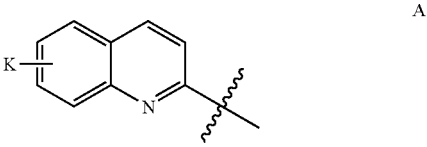

A

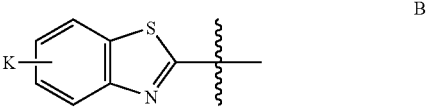

B

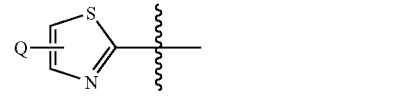

C

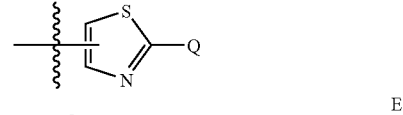

D

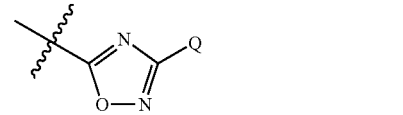

E

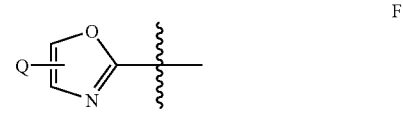

F

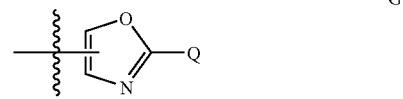

G

-continued

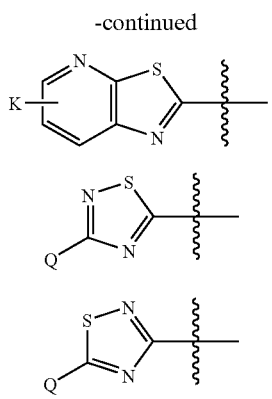

wherein K is (Alk$^2$)$_n$-Q,
wherein Alk$^2$ are optionally substituted C$_1$-C$_6$ alkylene, C$_2$-C$_6$ alkenylene, or C$_2$-C$_6$ alkynylene radicals, which may optionally terminate with or be interrupted by —O—, —S—, —S(O)—, —S(O$_2$)—, —NH—, —N(CH$_3$)—, or —N(CH$_2$CH$_3$)—; and
wherein Q is hydrogen, halogen, nitrile, or hydroxyl or an optionally substituted monocyclic carbocyclic or heterocyclic radical having 3 to 6 ring atoms; or an optionally substituted bicyclic carbocyclic or heterocyclic radical having 5 to 10 ring atoms; and
wherein n is 0 or 1, and wherein any unsubstituted ring carbon is optionally substituted,
R$_4$ and R$_5$ are independently fluoro or chloro, or one of R$_4$ and R$_5$ is hydrogen while the other is fluoro or chloro; and
R$_2$, R$_6$ and R$_7$ are independently hydrogen or a radical of formula -(Alk$^3$)x-(Z$^2$)y-(Alk$^4$)$_z$-H wherein x, y and z are independently 0 or 1,
Z$^2$ is —O—, —S—, —S(O)—, —S(O$_2$)—, —NH—, —N(CH$_3$)—, —N(CH$_2$CH$_3$)—, —C(=O)—, —O—(C=O)— or —C(=O)—O—;
Alk$_3$ and Alk$_4$ are optionally substituted C$_1$-C$_3$ alkylene, C$_2$-C$_3$ alkenylene, or C$_2$-C$_3$ alkynylene radicals, which may optionally terminate with or be interrupted by —O—, —S—, —S(O)—, —S(O$_2$)—, —NH—, —N(CH$_3$)—, or —N(CH$_2$CH$_3$)—.

2. A compound as claimed in claim 1 wherein W is =CH—.

3. A compound as claimed in claim 1 wherein R$_6$ and R$_7$ are each hydrogen.

4. A compound as claimed in claim 1 wherein R$_2$ is —OR$_8$, —OC(=O)R$_8$ or —SO$_2$R$_8$ wherein R$_8$ is optionally substituted C$_1$-C$_3$ alkyl or C$_2$-C$_3$ alkenyl.

5. A compound as claimed in claim 1 wherein R$_2$ is hydrogen, —OH, —OCH$_3$, —OC(=O)CH$_3$ Or —SO$_2$CH$_3$.

6. A compound as claimed in claim 1 wherein the length of the radical R$_3$ does not exceed the length of an unbranched saturated hydrocarbon chain of 14 carbon atoms.

7. A compound as claimed in claim 1 wherein the length of the radical R3 is equivalent to that of an unbranched saturated hydrocarbon chain of from 6 to 12, or 9 to 12 carbon atoms.

8. A compound as claimed in claim 1 wherein any optional substituents in R$_3$ are selected from methyl, —OCH$_3$, —CF$_3$, —OCF$_3$, ethyl, cyclopropyl, oxo, hydroxyl, —F, —Cl, —Br, cyano, acetyl, amino, methylamino, dimethylamino, acetylamino, carbamate, —CONH$_2$, nitro, —COOH and —CH$_2$OH.

9. A compound as claimed in claim 1 wherein Q is optionally substituted phenyl.

10. A compound as claimed in claim 1 wherein Q is optionally substituted pyridin-2-yl or pyridin-3-yl.

11. A compound as claimed in claim 1 wherein any optional substituents in Q are selected from methyl, —OCH$_3$, —CF$_3$, —OCF$_3$, ethyl, cyclopropyl, oxo, hydroxyl, —F, —Cl, —Br, cyano, acetyl, amino, methylamino, dimethylamino, acetylamino, carbamate, —CONH$_2$, nitro, —COOH and —CH$_2$OH.

12. A compound selected from the group consisting of:

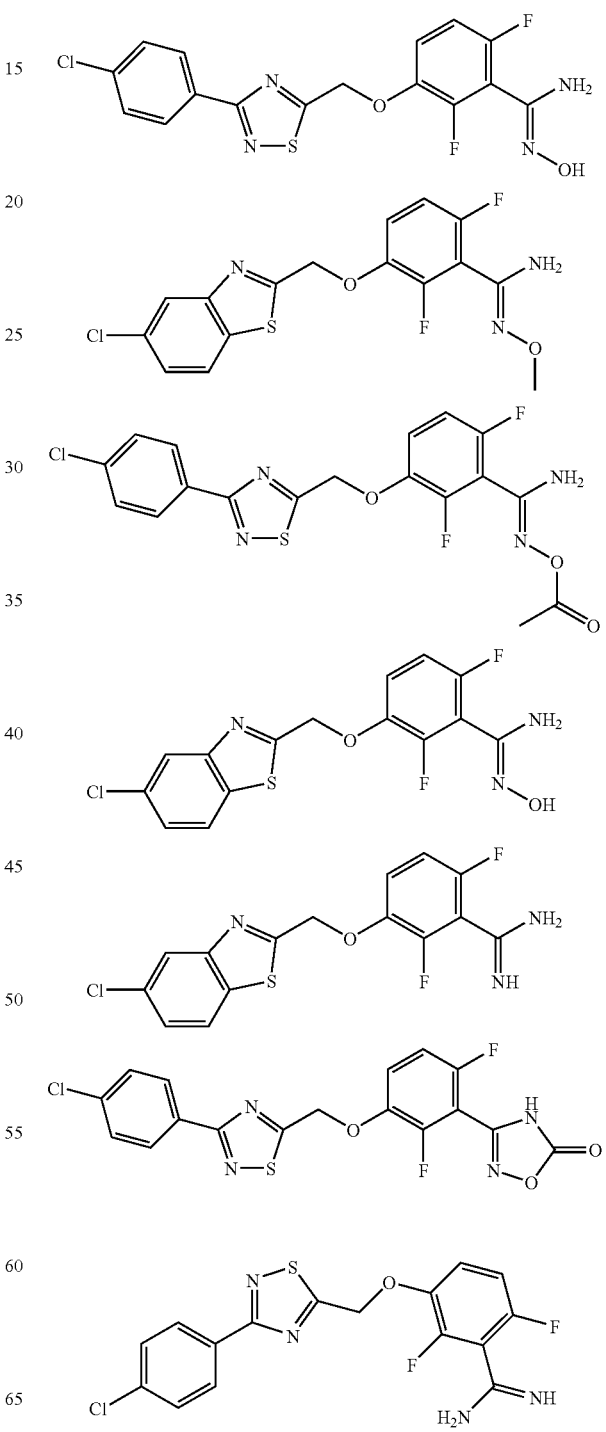

-continued

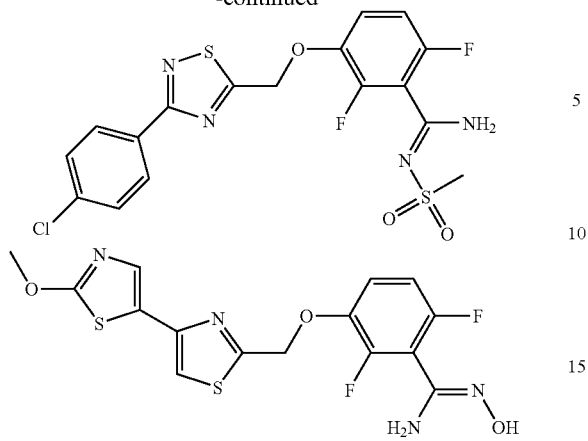

and salts thereof.

13. A pharmaceutical composition comprising a compound as claimed in claim 1 together with a pharmaceutically acceptable carrier.

14. An antibacterial composition comprising a compound as claimed in claim 1 in an amount effective to inhibit bacterial growth, together with a pharmaceutically acceptable carrier.

15. A compound as claimed in claim 1, for use in a method of treatment of the human or animal body.

* * * * *

UNITED STATES PATENT AND TRADEMARK OFFICE
CERTIFICATE OF CORRECTION

| | | |
|---|---|---|
| PATENT NO. | : 8,415,383 B2 | Page 1 of 1 |
| APPLICATION NO. | : 12/679334 | |
| DATED | : April 9, 2013 | |
| INVENTOR(S) | : David John Haydon et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 384 days.

In the Claims:

Column 30; Claim 1; Line 2:
Please delete "(1A)" and insert --(IA)--

Signed and Sealed this
Twentieth Day of August, 2013

Teresa Stanek Rea
*Acting Director of the United States Patent and Trademark Office*

UNITED STATES PATENT AND TRADEMARK OFFICE
CERTIFICATE OF CORRECTION

PATENT NO.       : 8,415,383 B2                                                                 Page 1 of 1
APPLICATION NO. : 12/679334
DATED            : April 9, 2013
INVENTOR(S)      : Haydon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 427 days.

Signed and Sealed this
First Day of September, 2015

Michelle K. Lee
*Director of the United States Patent and Trademark Office*